(12) United States Patent
Agar et al.

(10) Patent No.: US 10,689,639 B2
(45) Date of Patent: Jun. 23, 2020

(54) TETHERING CYSTEINE RESIDUES USING CYCLIC DISULFIDES

(71) Applicant: Brandeis University, Waltham, MA (US)

(72) Inventors: Jeffrey N. Agar, Newton, MA (US); Joseph Salisbury, Cranston, RI (US)

(73) Assignee: Brandeis University, Waltham, MA (US)

( * ) Notice: Subject to any disclaimer, the term of this patent is extended or adjusted under 35 U.S.C. 154(b) by 0 days.

(21) Appl. No.: 15/912,197

(22) Filed: Mar. 5, 2018

(65) Prior Publication Data

US 2018/0245063 A1 Aug. 30, 2018

Related U.S. Application Data

(62) Division of application No. 15/219,807, filed on Jul. 26, 2016, now Pat. No. 9,944,919, which is a division of application No. 14/440,978, filed as application No. PCT/US2013/070239 on Nov. 15, 2013, now Pat. No. 9,428,589.

(60) Provisional application No. 61/726,776, filed on Nov. 15, 2012.

(51) Int. Cl.
| | |
|---|---|
| *C12N 9/96* | (2006.01) |
| *C12N 9/02* | (2006.01) |
| *A61K 31/095* | (2006.01) |
| *A61K 31/385* | (2006.01) |
| *C07K 19/00* | (2006.01) |

(52) U.S. Cl.
CPC .............. *C12N 9/96* (2013.01); *A61K 31/095* (2013.01); *A61K 31/385* (2013.01); *C07K 19/00* (2013.01); *C12N 9/0089* (2013.01); *C12Y 115/01001* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 6,013,663 | A | 1/2000 | Fujita et al. |
| 6,046,228 | A | 4/2000 | Rice et al. |
| 9,944,919 | B2 * | 4/2018 | Agar .................... C12N 9/0089 |
| 2010/0093977 | A1 | 4/2010 | Baker et al. |
| 2010/0317608 | A1 | 12/2010 | Garner et al. |
| 2012/0134978 | A1 | 5/2012 | Agar |

FOREIGN PATENT DOCUMENTS

| | | |
|---|---|---|
| WO | 2005075513 A1 | 8/2005 |
| WO | 2010141613 A1 | 12/2010 |

OTHER PUBLICATIONS

Auclair et al., "Strategies for Stabilizing Superoxide Dismutase (SOD1), the Protein Destabilized in the Most Common Form of Familial Amyotrophic Lateral Sclerosis", Proceedings of the National Academy of Sciences, vol. 107, No. 50, Dec. 14, 2010, pp. 21394-21399, XP055266790, US.
Erlanson et al., "Tethering: Fragment-Based Drug Discovery", Jan. 1, 2009, XP055266987, Retrieved from the Internet: URL:http://www-nmr.cabm.rutgers.edu/academics/biochem694/2009BioChem412/2009Presentations/CurtSchauder.pdf [retrieved on Apr. 20, 2016].
Erlanson et al., "Tethering: Fragment-Based Drug Discovery", Annual Review of Biophysics and Biomolecular Structure, Annual Reviews Inc., Palo Alto, CA, US, vol. 33, Jan. 1, 2004, pp. 199-223, XP008069432.
European Search Report from EP 13854478.8, dated May 4, 2016.
Hardy, "Chapter 17. A Link Means a Lot: Disulfide Tethering in Structure-Based Drug Design" In: "Computational and Structural Approaches to Drug Discovery Ligand-Protein Interactions", Jan. 1, 2007, Royal Society of Chemistry, Cambridge, UK, XP055266983.
International Search Report dated May 12, 2014, from PCT/US2013/070239.
Isaac et al., "Nucleophilic Reactivity of Zinc-bound Thiolates: Subtle Interplay Between Coordination Set and Conformational Flexibility", Chemical Science, vol. 3, No. 12, Jan. 1, 2012, p. 3409, XP055266928, United Kingdom.
Japanese Office Action dated Oct. 24, 2017 in Japanese Application No. 2015-542801.
Logan et al., "Engineered Disulfide Bonds Restores Chaperone Like Function of DJ-1 Mutants Linked to Familial Parkinson's Disease," Biochemistry, 49(27):5624-5633 (2010).
Williams, B. "Disulfide-Mediated Stabilization of DJ-1, a Protein Implicated in Parkinson Disease" Honors Thesis, May 1, 2013 (May 1, 2013), XP055308842, Retrieved from the Internet: URL:http://bir.brandeis.edu/bitstream/handle/10192/25232/WilliamsThesis2013.pdf?sequence=I [retrieved on Oct. 10, 2016] the whole document.
Written Opinion of the International Search Authority dated May 12, 2014 in PCT/US2013/070239.
Canadian Office Action dated Jul. 25, 2019 received in corresponding CA Application 2,891,261.

* cited by examiner

Primary Examiner — Iqbal H Chowdhury
(74) Attorney, Agent, or Firm — Michele M. Wales; Inhouse Patent Counsel, LLC

(57) ABSTRACT

Described herein are compounds and methods for tethering proteins. For example, dimers of proteins, including SOD1 and DJ-1, are described, where the dimers are formed by the covalent bonding of a cysteine on the first monomer to a cysteine on the second monomer via a cyclic disulfide linker. The covalently attached dimers exhibit increased stabilization.

16 Claims, 5 Drawing Sheets

Specification includes a Sequence Listing.

NSC54128

NSC72270

NSC56224

NSC72272

NSC62632

NSC185355

NSC624157

NSC90788

NSC663605

NSC212561

NSC5391

NSC72268

NSC56224

TETHERING CYSTEINE RESIDUES USING CYCLIC DISULFIDES

RELATED APPLICATIONS

This application is a Divisional Application of U.S. application Ser. No. 15/219,807 filed Jul. 26, 2016, now Issued as U.S. Pat. No. 9,944,919, which is a Divisional Application of U.S. patent application Ser. No. 14/440,978, filed May 6, 2015, now U.S. Pat. No. 9,428,589, which is a National Stage application of PCT/US13/070239, filed Nov. 15, 2013, which claims the benefit of priority to U.S. Provisional Patent Application Ser. No. 61/726,776, filed Nov. 15, 2012. All of these documents are hereby incorporated by reference in their entirety.

This invention was made with government support under R01 NS065263 and R01 NS071256 awarded by the National Institutes of Health. The government has certain rights in the invention.

BACKGROUND OF THE INVENTION

Many therapeutic molecules form covalent bonds with cysteine residues on their protein targets. The mechanisms of the majority of these molecules were either elucidated long after development or are not fully understood. Recent successful drug discovery efforts, however, moved to structure-based design. These require both an accurate structural model of the target protein and a high-specificity ligand.

One third of therapeutic molecules, including many blockbuster drugs, form covalent bonds with their targets. These electrophilic drugs generally bond to a nucleophilic amino acid, often serine or cysteine, on a target protein. Aspirin and penicillin (and their many derivatives) acylate serines and numerous drugs form covalent bonds with specific cysteines. These therapeutic agents are effective despite the potential for off-target reactions with hundreds of highly reactive, nucleophilic residues, which are often required for the function of essential proteins. A worst case scenario for reaction with the "wrong" nucleophile is nerve gases (e.g., Sarin, intravenous $LD_{50}$ ~30 µg/kg), which covalently modify the active site serine of acetylcholine esterase. On the other hand, comparable toxicity has been harnessed to selectively target cancer cells—bortezomib/Velcade ($LD_{100}$<250 µg/kg) selectively modifies an active site threonine of the proteasome. Unintended reaction with a highly reactive nucleophile isn't necessarily disastrous—it has led to a drug. The disulfide-containing substance, disulfiram, was intended to treat parasitic infections, but when tested on humans gave severe "hangover" symptoms upon alcohol consumption. Years after its therapeutic use began, this compound, dubbed antabuse, was found to bind the highly reactive active site cysteines of alcohol dehydrogenase. Nevertheless, the paucity of therapeutic suicide inhibitors to most human proteases, which (unlike viral proteases) have numerous homologues with identical off-target catalytic sites, has been attributed to off-target nucleophiles.

With effective covalent drugs, off-target binding tends to be offset by selectivity for the target and the enhanced potency inherent to irreversible inhibition. The uncanny specificities of cysteine-binding therapeutics involve elegant and usually serendipitous chemistry. The gastroesophageal reflux disease drugs (GERD, e.g., omeprazole/Prilosec™, lansoprazole/Prevacid™, etc.) use a cyclic sulphenamide to irreversibly bind a cysteine residue of the proton pump of the intestinal lumen. These benzolamide-derivative prodrugs require protonation of a low pKa pyridine nitrogen (pKa<4.5) for activation and sequestration. They are neutral, inactive, and permeable, but are activated upon encountering the pH~0.8 parietal cell canaliculus, which contains their target (i.e., the proton pump). Here, they accumulate at 1000-fold higher concentrations. While the chemical basis of proton-mediated accumulation of omeprazole was appreciated, if not designed, the elegant sulfur-based chemistry behind activation and binding of a target cysteine was serendipitous.

The antithrombosis factors clopidogrel/Plavix™, ticlopide/Ticlid, etc. are also prodrugs. Activation by cytochrome P450 enzymes results in the scission of a ring carbon-sulfur bond, creating a sulfhydryl group that can then form a disulfide bond with its target cysteine on the adenosine diphosphate (ADP) chemoreceptor $P2Y_{12}$. In addition to increased specificity for its target, which it permanently inactivates, the active metabolite has improved plasma protein binding characteristics. The thrombosis drugs had their beginnings in functional assays, and fortunately animal studies, because the active metabolite is not produced in most cell-based assays. Both their mechanism of action and target were unknown at the time of discovery.

More recent compounds employing sulfhydryl moieties were rationally designed. Dacomitinib, afatinib, and neratinib are EGFR kinase inhibitors with a high-affinity, nucleotide-analogue moiety that reversibly binds the ATP-binding pockets of numerous kinases and a second moiety designed to covalently bond with a non-conserved cysteine (present in EGFR but not its homologues). The electrophilic moiety is purposefully a low-reactivity acrylamide to minimize off-target reactions. A related chemical approach used low-reactivity, acrylamide-based, electrophiles to target non-conserved (in humans) and non-catalytic-residue cysteine of the HCV NS3/4A viral protease (HCVP).

In sum, all known approaches either minimize the exposure of highly reactive electrophiles ("hiding" reactive sulfur in disulfides or in rings), or minimize the reactivity of exposed electrophiles (using acrylamide adducts). Unfortunately, however, the specificity of sulphenamides depends upon an acidic environment (pH<4.5) found only in the intestinal lumen, and the specificity of therapeutics employing reactive sulfhydryl groups is poorly understood. A few therapeutic molecules were obtained by rationally attaching low-reactivity electrophiles to high affinity and specificity moieties. Unfortunately, compounds with high affinity and specificity tend to appear in the final stages of a drug development effort making this approach best suited for improving existing specificity.

There exists a need for a strategy for conferring specificity to drugs that target cysteine, in general, but pairs of cysteine, in particular.

SUMMARY OF THE INVENTION

Representative Methods of the Invention

In certain embodiments, the invention relates to a method comprising the step of contacting a compound of Formula I or a compound of Formula II with a first protein and a second protein under conditions suitable for cross-linking the first protein to the second protein, thereby cross-linking the first protein to the second protein, wherein the first protein comprises a first cysteine residue;
the second protein comprises a second cysteine residue;
the compound of Formula I is

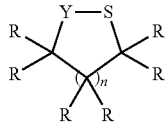

wherein

Y is S, S=O, or S(=O)$_2$;

n is 0, 1, 2, 3, or 4; and

R is independently selected from the group consisting of —H, —OH, —NH$_2$, —NHR', —N(R')$_2$, alkyl, —OMs, —OTs, —OTf, and —CO$_2$H; or any two geminal R groups, taken together, form an imine; or any two vicinal R groups, taken together, form a ring; wherein any alkyl or imine may be substituted with a carbamide, a carboxylate, or a hydroxyl; and R' is alkyl or aryl; and the compound of Formula II is

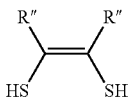

wherein

R" is —H, alkyl, or aryl, or both R", taken together, form a ring; wherein any alkyl, aryl, or ring may be substituted with —OH, alkyl, or halo.

In certain embodiments, the invention relates to a method comprising the step of contacting a compound with a first protein and a second protein under conditions suitable for cross-linking the first protein to the second protein, thereby cross-linking the first protein to the second protein, wherein the first protein and the second protein have at least 90% sequence homology;

the first protein and the second protein are SOD-1 or DJ-1; and the compound is a compound of Formula I

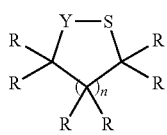

wherein

Y is S, S=O, or S(=O)$_2$;

n is 0, 1, 2, 3, or 4; and

R is independently selected from the group consisting of —H, —OH, —NH$_2$, —NHR', —N(R')$_2$, alkyl, —OMs, —OTs, —OTf, and —CO$_2$H; or any two geminal R groups, taken together, form an imine; or any two vicinal R groups, taken together, form a ring; wherein any alkyl or imine may be substituted with a carbamide, a carboxylate, or a hydroxyl; and R' is alkyl or aryl.

In certain embodiments, the invention relates to a method comprising the step of contacting a compound with a first protein and a second protein under conditions suitable for cross-linking the first protein to the second protein, thereby cross-linking the first protein to the second protein, wherein the first protein and the second protein have at least 90% sequence homology;

the first protein and the second protein are SOD-1 or DJ-1; and the compound is a compound of Formula II

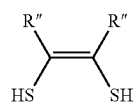

wherein

R" is —H, alkyl, or aryl, or both R", taken together, form a ring; wherein any alkyl, aryl, or ring may be substituted with —OH, alkyl, or halo.

In certain embodiments, the invention relates to a method of treating or preventing a condition, comprising the step of administering to a subject in need thereof a therapeutically effective amount of a compound of Formula I or a compound of Formula II, wherein the compound of Formula I is

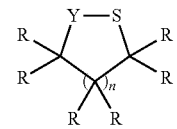

wherein

Y is S, S=O, or S(=O)$_2$;

n is 0, 1, 2, 3, or 4; and

R is independently selected from the group consisting of —H, —OH, —NH$_2$, —NHR', —N(R')$_2$, alkyl, —OMs, —OTs, —OTf, and —CO$_2$H; or any two geminal R groups, taken together, form an imine; or any two vicinal R groups, taken together, form a ring; wherein any alkyl or imine may be substituted with a carbamide, a carboxylate, or a hydroxyl; and R' is alkyl or aryl; and the compound of Formula II is

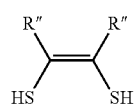

wherein

R" is —H, alkyl, or aryl, or both R", taken together, form a ring; wherein any alkyl, aryl, or ring may be substituted with —OH, alkyl, or halo.

In certain embodiments, the invention relates to a compound of Formula I

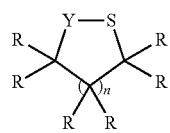

I wherein
  Y is S, S=O, or S(=O)$_2$;
  n is 0, 1, 2, 3, or 4; and
  R is independently selected from the group consisting of —H, —OH, —NH$_2$, —NHR', —N(R')$_2$, alkyl, —OMs, —OTs, —OTf, and —CO$_2$H; or any two geminal R groups, taken together, form an imine; or any two vicinal R groups, taken together, form a ring; wherein any alkyl or imine may be substituted with a carbamide, a carboxylate, or a hydroxyl; and
  R' is alkyl or aryl.

One aspect of the invention is a stabilized superoxide dismutase analogue, wherein said analogue has a tertiary structure and comprises a first SOD1 monomer and a second SOD1 monomer; wherein the first SOD1 monomer comprises a first cysteine residue; the second SOD1 monomer comprises a second cysteine residue; the first cysteine residue is connected to the second cysteine residue by a connection; and the connection is a connection of Formula III or Formula IV:

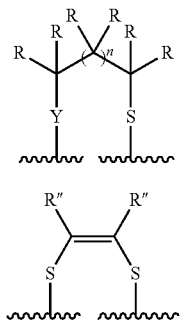

wherein
  Y is S, S=O, or S(=O)$_2$;
  n is 0, 1, 2, 3, or 4;
  R is independently selected from the group consisting of —H, —OH, —NH$_2$, —NHR', —N(R')$_2$, alkyl, —OMs, —OTs, —OTf, and —CO$_2$H; or any two geminal R groups, taken together, form an imine; or any two vicinal R groups, taken together, form a ring; wherein any alkyl or imine may be substituted with a carbamide, a carboxylate, or a hydroxyl; and
  R' is alkyl or aryl; and
  R" is —H, alkyl, or aryl, or both R", taken together, form a ring; wherein any alkyl, aryl, or ring may be substituted with —OH, alkyl, or halo.

One aspect of the invention is a stabilized DJ-1 analogue, wherein said analogue has a tertiary structure and comprises a first DJ-1 monomer and a second DJ-1 monomer; wherein the first DJ-1 monomer comprises a first cysteine residue; the second DJ-1 monomer comprises a second cysteine residue; the first cysteine residue is connected to the second cysteine residue by a connection; and the connection is a connection of Formula III or Formula IV:

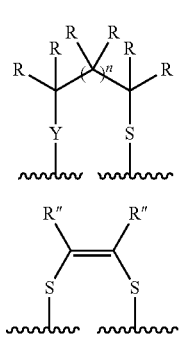

wherein
  Y is S, S=O, or S(=O)$_2$;
  n is 0, 1, 2, 3, or 4;
  R is independently selected from the group consisting of —H, —OH, —NH$_2$, —NHR', —N(R')$_2$, alkyl, —OMs, —OTs, —OTf, and —CO$_2$H; or any two geminal R groups, taken together, form an imine; or any two vicinal R groups, taken together, form a ring; wherein any alkyl or imine may be substituted with a carbamide, a carboxylate, or a hydroxyl; and
  R' is alkyl or aryl; and
  R" is —H, alkyl, or aryl, or both R", taken together, form a ring; wherein any alkyl, aryl, or ring may be substituted with —OH, alkyl, or halo.

BRIEF DESCRIPTION OF THE FIGURES

FIG. 1 depicts a) a potential reaction mechanism where a cyclic disulfide reacts with the cysteine of one monomer and the resulting thiolate can then react with, for example, a hydrogen peroxide-modified thiolate on the other monomer (Isaac, et al. Chemical Science 2012); b) side-chains of Cys53's in the dimer interface of DJ-1 (PDB: 3SF8) (SEQ ID NO:1), demonstrating their close spacing (Premkumar, et al. J. Struct. Biol. 2011, 176, 414). The appearance of Cys111's in the dimer interface of SOD1 is very similar.

DETAILED DESCRIPTION OF THE INVENTION

Overview

Figure 1:
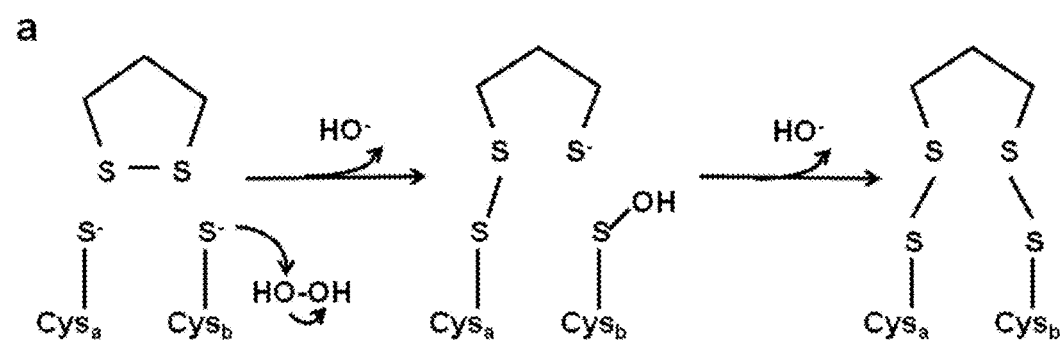
Figure 1:
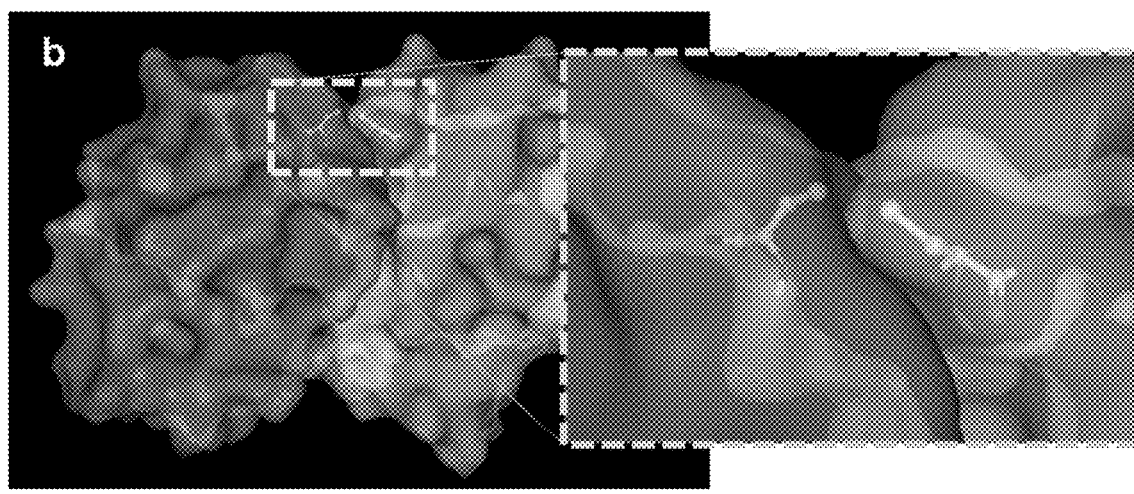

The covalent attachment of molecules can be used to affect protein structure and function. Covalently attached molecules can be used to inhibit, promote activity, stabilize, and destabilize proteins and peptides. One problem is encoding adequate specificity in covalent binders for the intended target. In certain embodiments, the invention relates to chemical tools, cyclic disulfides, that target pairs of cysteine residues and significantly enhance the specificity for pairs of cysteine over lone cysteine residues. In addition to augmenting current approaches to rational design, cyclic disulfides offer a launching point for compound optimization for novel targets. Whereas previous approaches to covalent modification tended to be devoted to inactivation of an enzyme, cyclic disulfides are also amenable to protein (including enzyme) stabilization. We apply cyclic-disulfides to the stabilization of two proteins involved in neurodegenerative disease, Cu/Zn-SOD1, which is involved in amyotrophic lateral sclerosis and potentially Parkinson's and Alzheimer's, and DJ-1, which is involved in Parkinson's.

SOD1 and Amyotrophic Lateral Sclerosis (ALS)

Amyotrophic lateral sclerosis is a progressive neurodegenerative disease caused by death of motor neurons in the brain and spinal cord. The overall median survival from onset of symptoms ranges between 2-3 years for cases with bulbar onset to 3-5 years for cases with limb onset. Lifetime risk of ALS is 1/400 to 1/1000 with a median annual incidence of 1.89 and a median prevalence of 5.2 per 100,000 each year. There exists no cure for ALS and the only FDA-approved treatment for ALS, riluzole (Rilutek), prolongs median survival by a mere 2-3 months when taken for an eighteen month duration. Thus, novel therapeutic strategies for ALS continue to be crucial. Approximately ten percent of ALS is familial (fALS) and approximately twenty percent of fALS cases are caused by autosomal dominant mutations in the ubiquitously expressed protein SOD1. Over 100 SOD1 mutations have been identified which are linked with fALS and it is thought they confer a toxic gain of function. As the clinical phenotypes of patients with various fALS SOD1-associated mutations are more alike than different, and all appear to cause the death of motor neurons, it has been hypothesized that mutations share common properties and mechanisms of cytotoxicity. In addition to causing twenty percent of fALS, SOD1 may be playing a role in sporadic ALS. Evidence is emerging that a subset of sporadic ALS is characterized by unfolded WT SOD1, and that oxidatively modified SOD1 slows axonal transport to a similar extent to the G93A SOD1 variant. Numerous other reports have also implicated oxidized/misfolded WT SOD1 as being cytotoxic and/or related to sporadic ALS.

One prevailing hypothesis for the mechanism of the toxicity of ALS-associated SOD1 variants involves dimer destabilization and dissociation into monomers, which then nucleate the formation of higher-order aggregates. ALS-associated variants of SOD1, such as G85R, are found as monomers in ALS patients and a number of modifications, including loss of Cu or Zn, cleavage of the native, intramolecular disulfide, oxidation, glutathionylation, and fALS-associated mutation, predispose the SOD1 dimer to dissociate. X-ray crystal structures of both A4V, and to a lesser extent I113T, yeast two-hybrid analysis of H46R, A4V, and H48Q, dissociation of G85R, G93R, E100G, and I113T by chaotrophs, and molecular dynamics simulations are all consistent with this hypothesis; mutations and modifications destabilize dimer formation. Furthermore, destabilization of dimer formation has been found to be reversible through both the tethering of subunits with a genetically engineered inter-subunit disulfide and the use of small molecules and this prevents protein aggregation. Thus, dimer stabilization is being pursued as a therapeutic strategy.

SOD1 dimers contain two cysteine residues at the dimer interface whose sulfhydryl groups are approximately nine angstroms apart. These sulfhydryl groups can be targeted by maleimide cross-linkers which lead to strong stabilization of ALS-associated SOD1 dimers. Surprisingly, while cross-linking at sulfhydryl groups by the maleimides occurred by predicted maleimide-mediated mechanisms, for the maleimide dithio-bismaleimidoethane (DTME), it was found that stabilization of the SOD1 dimer possibly occurred through both maleimide interaction with the sulfhydryl group of Cys111 on one SOD1 monomer as well as thiol-disulfide exchange between the disulfide spacer of DTME and the sulfhydryl group of the Cys111 on the second SOD1 monomer. Unfortunately, maleimides are highly irritating locally and have an $LD_{50}$ in mice of 9 mg/kg with renal, hepatic, neurologic and hematologic toxicities as the principal effects of the drug in this species. Therefore, in certain embodiments, the invention relates to the discovery of molecules that can cross-link SOD1 dimers in order to fully assess small molecule-mediated covalent dimer formation of SOD1 as a therapeutic strategy for ALS.

DJ-1 and Parkinson's Disease (PD)

The progressive neurodegenerative disorder PD is characterized by the loss of dopaminergic neurons in the substania nigra pars compacta and α-synuclein-rich protein deposits known as Lewy bodies. A variety of pharmacological treatment options exist for the early-stage symptoms of PD as the patient becomes functionally impaired. However, as the disease progresses, all of these agents, which primarily treat the symptoms of PD, become ineffective as fewer dopaminergic neurons survive. Thus, as the ability to slow the progression of the disease remains elusive, novel directions in therapeutic development are necessary to further combat PD.

While the majority (>90%) of PD cases are idiopathic, mutations in PARK7, encoding the 189-amino acid homodimeric protein DJ-1, are known to be a rare cause of autosomal recessive early-onset Parkinson disease. Some evidence also indicates polymorphisms in PARK7 confer risk in sporadic PD patients. Biochemical and cell culture analysis of PD-linked variants of DJ-1 suggest a number of mechanisms through which structural defects, including loss of stability and dimer formation, may lead to a loss-of-function that is associated with PD pathogenicity, such as reduced ability to prevent α-synuclein aggregation, deficiency in oxidative stress-dependent RNA-binding activity, reduced ability to act as a neuroprotective transcriptional co-activator, and increased sensitivity to oxidative stress-induced cell death related to mitochondrial defects. In additional to recessive PD-related mutants of DJ-1 being implicated in disease, analysis of DJ-1 in the frontal cortex of patients with sporadic PD and Alzheimer's disease reveal that acidic isoforms of monomeric DJ-1 and basic isoforms of SDS-resistant dimeric DJ-1 selectively accumulate in these diseases, with DJ-1 irreversibly oxidized by carbonylation as well as by methionine oxidation to methionine sulfone. Over-oxidation of DJ-1 has been found to produce structural destabilization similar to PD-related mutations, suggesting that dysfunctional DJ-1 due to aberrant modifications could be a cause of sporadic neurodegenerative cases.

Just as loss of DJ-1 function appears to contribute to the etiology of PD, evidence suggests that enhancement of DJ-1 function could compensate for other causes of PD. DJ-1 protects against degeneration of nigral dopaminergic neurons in PD rat models involving both 6-hydroxydopamine and rotenone treatment. Viral-mediated DJ-1 overexpression in the MPTP mouse model has also proved efficacious in reducing nigral dopamine neuron loss. Likewise, pharmacological upregulation of DJ-1 with the histone deacetylase inhibitor phenylbutyrate rescues cells from oxidative stress and mutant α-synuclein toxicity, as well as protects dopaminergic neurons from MPTP-induced neurotoxicity and prevents age-related motor and cognitive decline in mice with diffuse Lewy body disease. Thus, enhancement of DJ-1 activity could serve as a therapeutic strategy in a possibly wide variety of PD cases. Previously, in silico methods have been used to identify potential small molecule binding sites on DJ-1 and for identifying small molecules capable of interacting with DJ-1 and modulating its oxidation state that have neuroprotective effects in vivo. Amazingly, DJ-1 dimers have a set of cysteines, Cys53's, spaced closely together around the dimer interface similar to SOD1, suggesting covalent dimerization at these cysteines might also be possible. Enhancing dimer formation of DJ-1 at these cysteines has been conceptually demonstrated via an engineered disulfide bond produced by a V51C mutation in DJ-1, which rescues structural and functional defects due to modification and mutations. Interestingly, highly reactive dopamine quinones have been observed to form covalent dimers of DJ-1 via Cys53, a putative natural mechanism of covalent dimer stabilization of DJ-1. However, Cys53s in DJ-1 are more closely spaced than Cys111s in SOD1, hindering previous attempts to covalently dimerize DJ-1 using maleimide crosslinkers.

Dithiols and Cyclic Disulfides as Covalent Dimerizers and Therapeutics

With the observation that DTME was able to cross-link SOD1 monomers partially through thiol-disulfide exchange, we proposed that cyclic disulfides may provide an alternative for covalently dimerizing both SOD1 and DJ-1 through their respective closely spaced dimer interface cysteines. Theoretically, a cyclic disulfide could undergo thiol-disulfide exchange with the cysteine of one SOD1/DJ-1 monomer, leaving a free thiolate to react with the remaining monomer (FIG. 1). Dithiols might also be capable of forming covalent dimers if the thiol groups are properly spaced and appropriately reactive. In agreement with this hypothesis, we present several cyclic disulfides and a dithiol discovered in preliminary screens that are capable of covalently dimerizing SOD1 and/or DJ-1. Several cyclic disulfides are already known to be safe for human consumption and/or are potential therapeutics including 4,5-dihydroxy-1,2-dithiane and α-lipoic acid (ALA), suggesting more cyclic disulfides might also make feasible drug development candidates. Furthermore, while there remains a common apprehension against the development of covalently acting drugs for fear of indiscriminate reactivity, numerous examples exist of such drugs that have excellent safety records, with proven techniques existing to systematically rank lead compounds based on selectivity.

Representative Methods of the Invention

In certain embodiments, the invention relates to a method comprising the step of contacting a compound of Formula I or a compound of Formula II with a first protein and a second protein under conditions suitable for cross-linking the first protein to the second protein, thereby cross-linking the first protein to the second protein, wherein
the first protein comprises a first cysteine residue;
the second protein comprises a second cysteine residue;
the compound of Formula I is

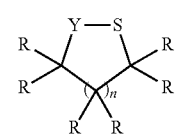

I wherein
Y is S, S=O, or S(=O)$_2$;
n is 0, 1, 2, 3, or 4; and
R is independently selected from the group consisting of —H, —OH, —NH$_2$, —NHR', —N(R')$_2$, alkyl, —OMs, —OTs, —OTf, and —CO$_2$H; or any two geminal R groups, taken together, form an imine; or any two vicinal R groups, taken together, form a ring; wherein any alkyl or imine may be substituted with a carbamide, a carboxylate, or a hydroxyl; and R' is alkyl or aryl; and
the compound of Formula II is

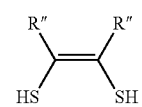

II wherein
R" is —H, alkyl, or aryl, or both R", taken together, form a ring; wherein any alkyl, aryl, or ring may be substituted with —OH, alkyl, or halo.

In certain embodiments, the invention relates to a method comprising the step of contacting a compound with a first protein and a second protein under conditions suitable for cross-linking the first protein to the second protein, thereby cross-linking the first protein to the second protein, wherein
the first protein and the second protein have at least 90% sequence homology;
the first protein and the second protein are SOD-1 or DJ-1; and
the compound is a compound of Formula I

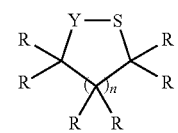

I wherein

Y is S, S=O, or S(=O)$_2$;

n is 0, 1, 2, 3, or 4; and

R is independently selected from the group consisting of —H, —OH, —NH$_2$, —NHR', =N(R')$_2$, alkyl, —OMs, —OTs, —OTf, and —CO$_2$H; or any two geminal R groups, taken together, form an imine; or any two vicinal R groups, taken together, form a ring; wherein any alkyl or imine may be substituted with a carbamide, a carboxylate, or a hydroxyl; and R' is alkyl or aryl.

In certain embodiments, the invention relates to any one of the aforementioned methods, wherein Y is S.

In certain embodiments, the invention relates to any one of the aforementioned methods, wherein Y is S=O.

In certain embodiments, the invention relates to any one of the aforementioned methods, wherein Y is S(=O)$_2$.

In certain embodiments, the invention relates to any one of the aforementioned methods, wherein n is 1 or 2.

In certain embodiments, the invention relates to any one of the aforementioned methods, wherein n is 1.

In certain embodiments, the invention relates to any one of the aforementioned methods, wherein n is 2.

In certain embodiments, the invention relates to any one of the aforementioned methods, wherein the compound is selected from the group consisting of

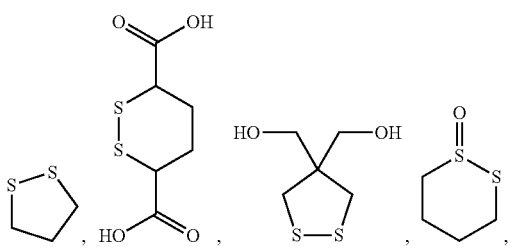

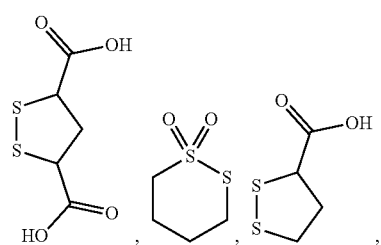

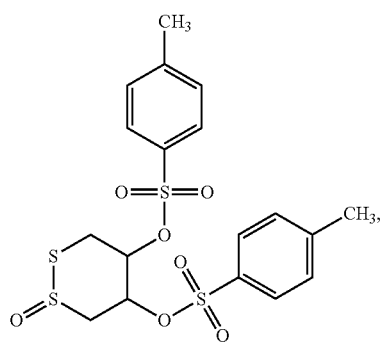

-continued

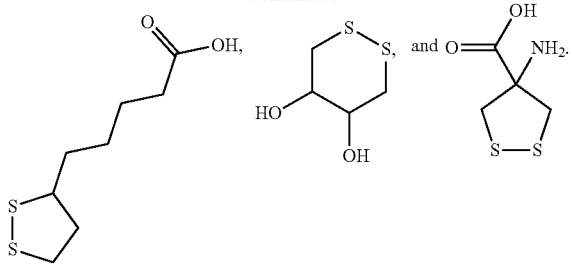

In certain embodiments, the invention relates to a method comprising the step of contacting a compound with a first protein and a second protein under conditions suitable for cross-linking the first protein to the second protein, thereby cross-linking the first protein to the second protein, wherein the first protein and the second protein have at least 90% sequence homology;

the first protein and the second protein are SOD-1 or DJ-1; and the compound is a compound of Formula II

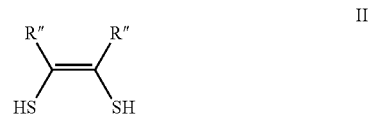

II wherein

R" is —H, alkyl, or aryl, or both R", taken together, form a ring; wherein any alkyl, aryl, or ring may be substituted with —OH, alkyl, or halo.

In certain embodiments, the invention relates to any one of the aforementioned methods, wherein the R" form a six-membered ring. In certain embodiments, the invention relates to any one of the aforementioned methods, wherein the R" form an aromatic ring. In certain embodiments, the invention relates to any one of the aforementioned methods, wherein the R" form a six-membered aromatic ring.

In certain embodiments, the invention relates to any one of the aforementioned methods, wherein the compound is

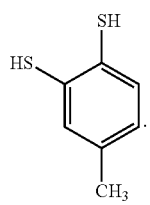

In certain embodiments, the invention relates to any one of the aforementioned methods, wherein the first protein and the second protein have at least 95% sequence homology.

In certain embodiments, the invention relates to any one of the aforementioned methods, wherein the first protein and the second protein have at least 98% sequence homology.

In certain embodiments, the invention relates to any one of the aforementioned methods, wherein the first protein and the second protein have at least 99% sequence homology.

In certain embodiments, the invention relates to any one of the aforementioned methods, wherein the first protein and the second protein are wild type SOD-1.

In certain embodiments, the invention relates to any one of the aforementioned methods, wherein the first protein and the second protein are wild type DJ-1.

In certain embodiments, the invention relates to any one of the aforementioned methods, wherein the method is in vitro. In certain embodiments, the invention relates to any one of the aforementioned methods, wherein the first protein and the second protein are in a cell.

In certain embodiments, the invention relates to any one of the aforementioned methods, wherein the method is a method of inhibiting the activity of the first protein or the second protein.

In certain embodiments, the invention relates to any one of the aforementioned methods, wherein the method is a method of increasing the activity of the first protein or a second protein.

In certain embodiments, the invention relates to any one of the aforementioned methods, wherein the method is a method of stabilizing the first protein or the second protein.

In certain embodiments, the invention relates to any one of the aforementioned methods, wherein the method is a method of destabilizing the first protein or the second protein.

In certain embodiments, the invention relates to a method of treating or preventing a condition, comprising the step of administering to a subject in need thereof a therapeutically effective amount of a compound of Formula I or a compound of Formula II,
wherein
the compound of Formula I is

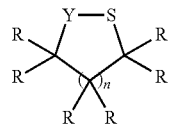

I wherein
Y is S, S=O, or S(=O)$_2$;
n is 0, 1, 2, 3, or 4; and
R is independently selected from the group consisting of —H, —OH, —NH$_2$, —NHR', —N(R')$_2$, alkyl, —OMs, —OTs, —OTf, and —CO$_2$H; or any two geminal R groups, taken together, form an imine; or any two vicinal R groups, taken together, form a ring; wherein any alkyl or imine may be substituted with a carbamide, a carboxylate, or a hydroxyl; and
R' is alkyl or aryl; and
the compound of Formula II is

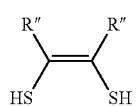

II wherein
R" is —H, alkyl, or aryl, or both R", taken together, form a ring; wherein any alkyl, aryl, or ring may be substituted with —OH, alkyl, or halo.

In certain embodiments, the invention relates to any one of the aforementioned methods, wherein the compound is a compound of Formula I; and Y is S.

In certain embodiments, the invention relates to any one of the aforementioned methods, wherein the compound is a compound of Formula I; and Y is S=O.

In certain embodiments, the invention relates to any one of the aforementioned methods, wherein the compound is a compound of Formula I; and Y is S(=O)$_2$.

In certain embodiments, the invention relates to any one of the aforementioned methods, wherein the compound is a compound of Formula I; and n is 1 or 2.

In certain embodiments, the invention relates to any one of the aforementioned methods, wherein the compound is a compound of Formula I; and n is 1.

In certain embodiments, the invention relates to any one of the aforementioned methods, wherein the compound is a compound of Formula I; and n is 2.

In certain embodiments, the invention relates to any one of the aforementioned methods, wherein the compound is the compound is a compound of Formula I; and the compound is selected from the group consisting of

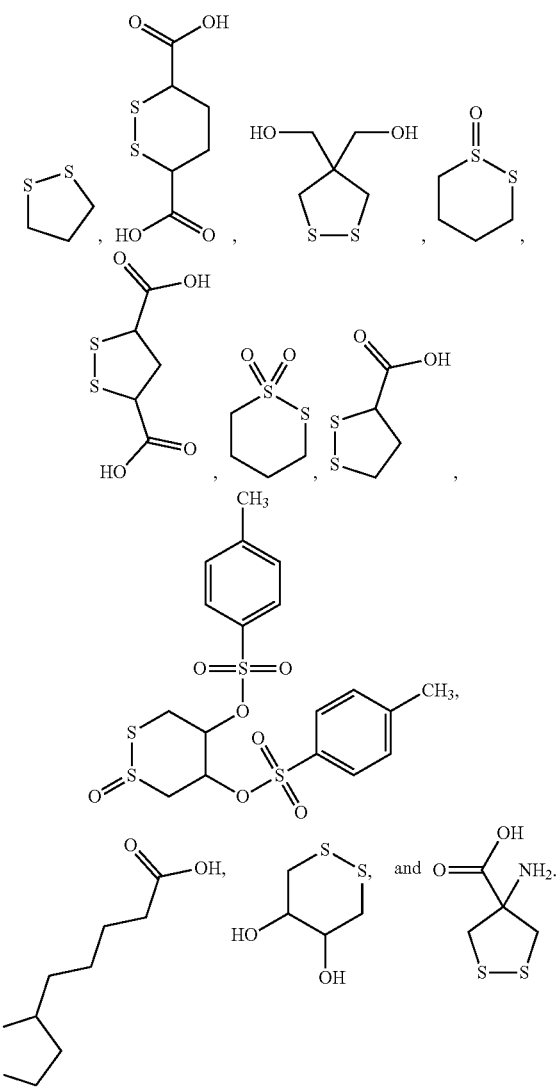

In certain embodiments, the invention relates to any one of the aforementioned methods, wherein the compound is a compound of Formula II; and the R" form a six-membered ring. In certain embodiments, the invention relates to any one of the aforementioned methods, wherein the compound is a compound of Formula II; and the R″ form an aromatic ring. In certain embodiments, the invention relates to any one of the aforementioned methods, wherein the compound is a compound of Formula II; and the R″ form a six-membered aromatic ring.

In certain embodiments, the invention relates to any one of the aforementioned methods, wherein the compound is a compound of Formula II; and the compound is

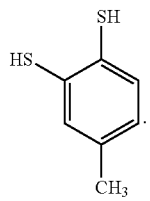

In certain embodiments, the invention relates to any one of the aforementioned methods, wherein the condition is ALS, Parkinson's disease, or Alzheimer's disease.

Representative Compounds of the Invention

In certain embodiments, the invention relates to a compound of Formula I

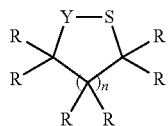

I wherein
Y is S, S=O, or S(=O)$_2$;
n is 0, 1, 2, 3, or 4; and
R is independently selected from the group consisting of —H, —OH, —NH$_2$, —NHR′, —N(R′)$_2$, alkyl, —OMs, —OTs, —OTf, and —CO$_2$H; or any two geminal R groups, taken together, form an imine; or any two vicinal R groups, taken together, form a ring; wherein any alkyl or imine may be substituted with a carbamide, a carboxylate, or a hydroxyl; and
R′ is alkyl or aryl.

In certain embodiments, the invention relates to any one of the aforementioned compounds, wherein Y is S.

In certain embodiments, the invention relates to any one of the aforementioned compounds, wherein Y is S=O.

In certain embodiments, the invention relates to any one of the aforementioned compounds, wherein Y is S(=O)$_2$.

In certain embodiments, the invention relates to any one of the aforementioned compounds, wherein n is 1 or 2.

In certain embodiments, the invention relates to any one of the aforementioned compounds, wherein n is 1.

In certain embodiments, the invention relates to any one of the aforementioned compounds, wherein n is 2.

In certain embodiments, the invention relates to any one of the aforementioned compounds, wherein the proviso that the compound is not selected from the group consisting of

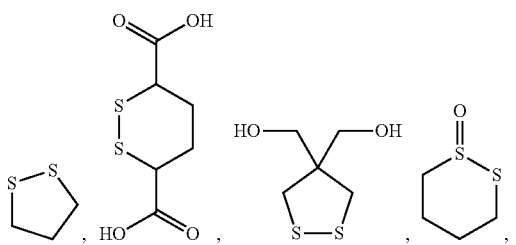

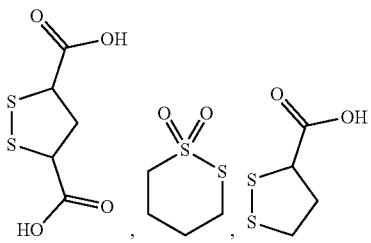

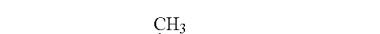

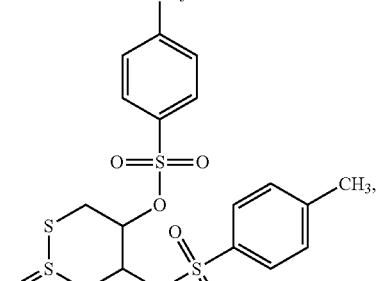

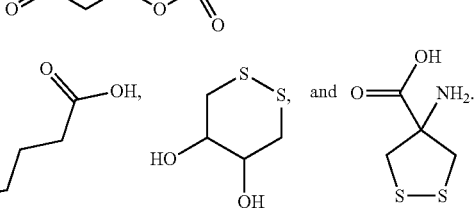

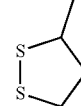

Representative Analogues of the Invention

One aspect of the invention is a stabilized superoxide dismutase analogue, wherein said analogue has a tertiary structure and comprises a first SOD1 monomer and a second SOD1 monomer; wherein the first SOD1 monomer comprises a first cysteine residue; the second SOD1 monomer comprises a second cysteine residue; the first cysteine residue is connected to the second cysteine residue by a connection; and the connection is a connection of Formula III or Formula IV:

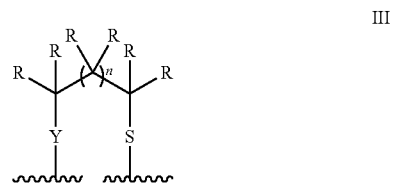

III

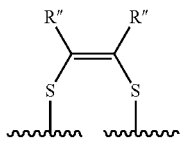

IV wherein
Y is S, S=O, or S(=O)$_2$;
n is 0, 1, 2, 3, or 4;
R is independently selected from the group consisting of —H, —OH, —NH$_2$, —NHR', —N(R')$_2$, alkyl, —OMs, —OTs, —OTf, and —CO$_2$H; or any two geminal R groups, taken together, form an imine; or any two vicinal R groups, taken together, form a ring; wherein any alkyl or imine may be substituted with a carbamide, a carboxylate, or a hydroxyl; and R' is alkyl or aryl; and R" is —H, alkyl, or aryl, or both R", taken together, form a ring; wherein any alkyl, aryl, or ring may be substituted with —OH, alkyl, or halo.

In certain embodiments, the present invention relates to any one of the aforementioned analogues, wherein the tertiary structure is substantially the same as the wild-type superoxide dismutase enzyme.

In certain embodiments, the present invention relates to any one of the aforementioned analogues, wherein the sequence homology of said first SOD1 monomer and said second SOD1 monomer is greater than or equal to about 85%.

In certain embodiments, the present invention relates to any one of the aforementioned analogues, wherein said first SOD1 monomer and said second SOD1 monomer have substantially the same amino acid sequence.

In certain embodiments, the present invention relates to any one of the aforementioned analogues, wherein the first SOD1 monomer of said analogue is the wild-type sequence or comprises a mutation selected from the group consisting of G93A, G85R, D90A, A4V, E100G, H46R, C6G, and I113T.

In certain embodiments, the present invention relates to any one of the aforementioned analogues, wherein the second SOD1 monomer of said analogue is the wild-type sequence or comprises a mutation selected from the group consisting of G93A, G85R, D90A, A4V, E100G, H46R, C6G, and I113T.

In certain embodiments, the present invention relates to any one of the aforementioned analogues, wherein said analogue retains at least 90% activity of the wild-type superoxide dismutase enzyme up to a temperature of about 75° C.

One aspect of the invention is a stabilized DJ-1 analogue, wherein said analogue has a tertiary structure and comprises a first DJ-1 monomer and a second DJ-1 monomer; wherein the first DJ-1 monomer comprises a first cysteine residue; the second DJ-1 monomer comprises a second cysteine residue; the first cysteine residue is connected to the second cysteine residue by a connection; and the connection is a connection of Formula III or Formula IV:

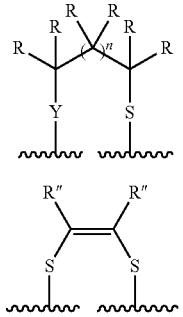

wherein
Y is S, S=O, or S(=O)$_2$;
n is 0, 1, 2, 3, or 4;
R is independently selected from the group consisting of —H, —OH, —NH$_2$, —NHR', —N(R')$_2$, alkyl, —OMs, —OTs, —OTf, and —CO$_2$H; or any two geminal R groups, taken together, form an imine; or any two vicinal R groups, taken together, form a ring; wherein any alkyl or imine may be substituted with a carbamide, a carboxylate, or a hydroxyl; and R' is alkyl or aryl; and R" is —H, alkyl, or aryl, or both R", taken together, form a ring; wherein any alkyl, aryl, or ring may be substituted with —OH, alkyl, or halo.

In certain embodiments, the present invention relates to any one of the aforementioned analogues, wherein the tertiary structure is substantially the same as the wild-type DJ-1.

In certain embodiments, the present invention relates to any one of the aforementioned analogues, wherein the sequence homology of said first DJ-1 monomer and said second DJ-1 monomer is greater than or equal to about 85%.

In certain embodiments, the present invention relates to any one of the aforementioned analogues, wherein said first DJ-1 monomer and said second DJ-1 monomer have substantially the same amino acid sequence.

In certain embodiments, the present invention relates to any one of the aforementioned analogues, wherein said analogue retains at least 90% activity of the wild-type DJ-1 up to a temperature of about 75° C.

In certain embodiments, the present invention relates to any one of the aforementioned analogues, wherein said analogue is increased in stabilization from about 10° C. to about 60° C.

In certain embodiments, the present invention relates to any one of the aforementioned analogues, wherein said analogue is increased in stabilization from about 20° C. to about 40° C.

In certain embodiments, the present invention relates to any one of the aforementioned analogues, wherein said analogue is increased in stabilization from about 15° C. to about 25° C.

In certain embodiments, the present invention relates to any one of the aforementioned analogues, wherein said analogue is increased in stabilization from about 30° C. to about 50° C.

In certain embodiments, the present invention relates to any one of the aforementioned analogues, wherein said analogue is increased in stabilization about 20° C.

In certain embodiments, the present invention relates to any one of the aforementioned analogues, wherein said analogue is increased in stabilization about 40° C.

Definitions

The term "analogue" refers to a molecule substantially similar in function to SOD1 protein or a fragment thereof.

The terms "percent (%) amino acid sequence identity" or "percent amino acid sequence homology" or "percent (%) identical" as used herein with respect to a reference polypeptide is defined as the percentage of amino acid residues in a candidate polypeptide sequence that are identical with the amino acid residues in the reference polypeptide sequence after aligning the sequences and introducing gaps, if necessary, to achieve the maximum percent sequence identity, without considering any conservative substitutions as part of the sequence identity. Alignment for the purpose of determining percent amino acid sequence identity can be achieved by various techniques known in the art, for instance, using publicly available computer software such as ALIGN or Megalign (DNASTAR). Those skilled in the art can determine appropriate parameters for measuring alignment, including any algorithms needed to achieve maximal alignment over the full length of the peptide sequence being used in the comparison. For example, in the context of the present invention, an analogue of SOD1 is said to share "substantial homology" with SOD1 if the amino acid sequence of said analogue is at least about 85%, at least about 90%, at least about 95%, or at least about 99% identical to wild-type.

The phrase "pharmaceutically acceptable" is employed herein to refer to those ligands, materials, compositions, and/or dosage forms which are, within the scope of sound medical judgment, suitable for use in contact with the tissues of human beings and animals, substantially non-pyrogenic, without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject chemical from one organ or portion of the body, to another organ or portion of the body. Each carrier must be "acceptable" in the sense of being compatible with the other ingredients of the formulation, not injurious to the patient, and substantially non-pyrogenic. Some examples of materials which can serve as pharmaceutically acceptable carriers include: (1) sugars, such as lactose, glucose, and sucrose; (2) starches, such as corn starch and potato starch; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

A "therapeutically effective amount" of a compound, e.g., such as a polypeptide or peptide analogue of the present invention, with respect to use in treatment, refers to an amount of the polypeptide or peptide in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

The terms "prophylactic" or "therapeutic" treatment are art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

EXEMPLIFICATION

The invention now being generally described, it will be more readily understood by reference to the following examples which are included merely for purposes of illustration of certain aspects and embodiments of the present invention, and are not intended to limit the invention.

Example 1

General Materials and Methods

Cross-Linking and Western Blots

WtSOD1 or wtDJ-1 was incubated with 5-25 mM DTT for approximately 20 minutes and either buffer exchanged using Amicon Ultra-4 centrifugal spin concentrators (MWCo 10K) or using reversed phase chromatography (ZIPTIP, Millipore, Inc). Samples cleaned by ZIPTIPs were also subjected to incubation with 5 mM EDTA. SOD1 samples that were buffer exchanged using Amicon concentrators were exchanged into in HPLC water, whereas ZIPTIP samples were further exchanged after ZIPTIP into PBS, pH 7.4 or HPLC water. DTT-reduced SOD1 or DJ-1 was incubated at a 1:1 (20 µM:20 µM or 10 µM:10 µM) or 1:3 (20 µM:60 µM or 10 µM:30 µM) ratio of protein to cross-linker.

A variety of cross-linkers were used. Cross-linking was achieved by incubating the reaction in either PBS pH 7.4 or water at room temperature for 1 hour. After an hour the reactions were analyzed on a 15% SDS-PAGE gel with a non-cross-linked control, transferred to nitrocellulose membrane and western blotted using a polyclonal antibody to SOD1 or DJ-1. Repeated in triplicate.

In addition, DTME is a cleavable sulfhydryl-sulfhydryl cross-linking agent. Therefore, a cross-linking reaction containing 1:1 molar ration of wtSOD1 or wtDJ-1 to DTME was performed at room temperature for one hour. After cross-linking, the reaction was split in half and half of the sample was run in a sample buffer containing DTT (reducing) and the other half in one containing no DTT (non-reducing). These samples along with non-cross-linked controls were then analyzed on a 15% SDS PAGE gel and western blotted as above.

Matrix Assisted Laser Desorption Ionization (MALDI)-Time Of Flight (TOF)

wtSOD1 or wtDJ-1 was cross-linked as below. After cross-linking, 1 µL of sample was spotted on a MALDI target containing 1 µl of matrix, 20 mg/mL sinipic acid, and analyzed on a Bruker Daltonics Microflex. The MALDI was calibrated each time using a high molecular weight protein calibration standard, Protein Calibration Standard I (Bruker Daltonics). The MALDI-TOF was operated in linear mode using a laser power of between 72-90%. MALDI-TOF spectra were of cross-linked and non-cross-linked samples were analyzed using FlexAnalysis software (Bruker Daltonics). Repeated in triplicate.

Example 2

Figure 2:
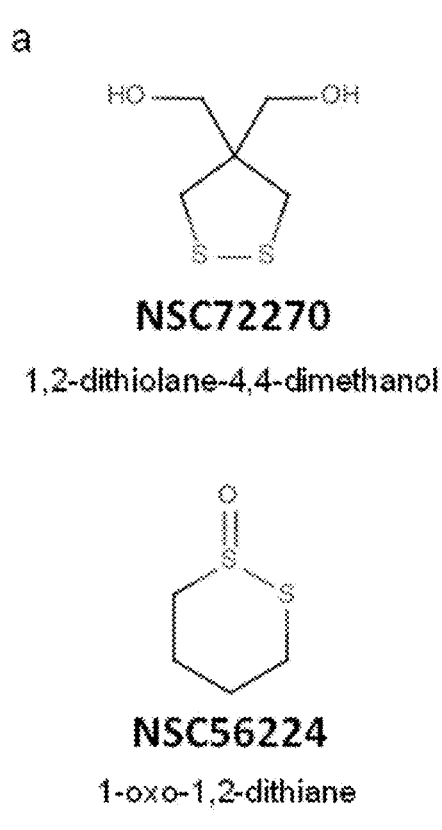
FIG. 2 depicts a preliminary LC-ESI-IonTrap-MS screen of cyclic disulfides that identifies multiple compounds that form covalent SOD1 dimers. a) Cyclic disulfides identified in our preliminary screen that form covalent-linked SOD1 dimers. b) Deconvoluted LC-MS spectra of SOD1 with no compound (top) and with 1-oxo-1,2-dithiane (bottom).
Figure 2:
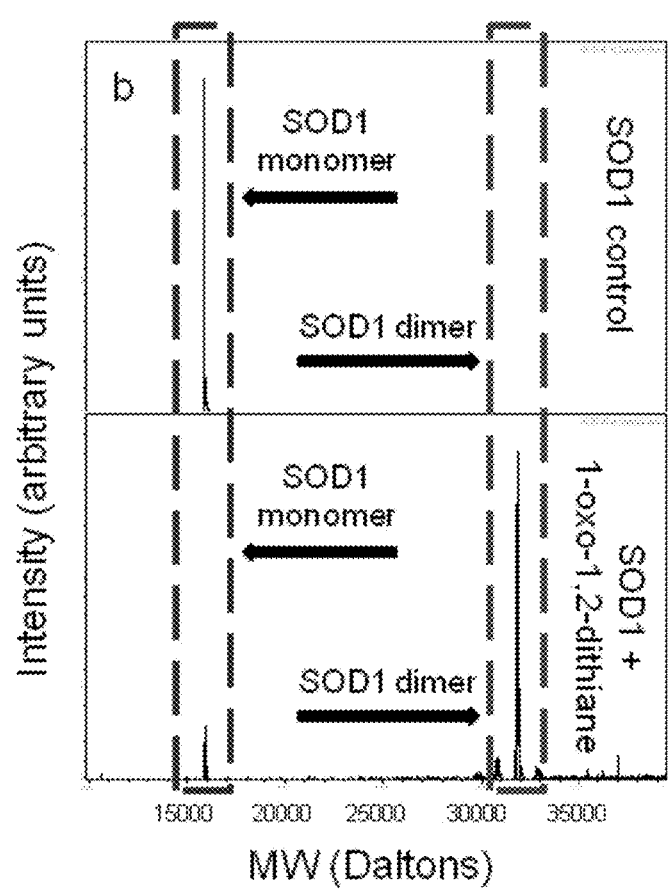
Figure 4:
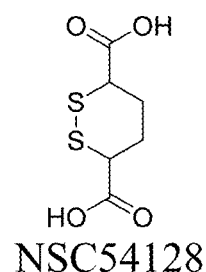
FIG. 4 depicts examples of cyclic disulfide compounds that are able to form covalent dimers of SOD1.
Figure 4:
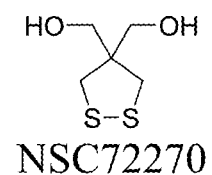
Figure 4:
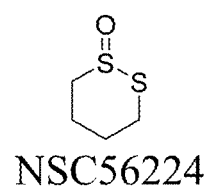
Figure 4:
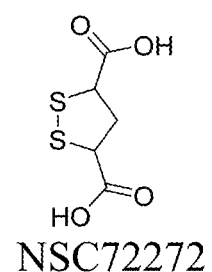
Figure 4:
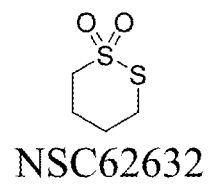
Figure 4:
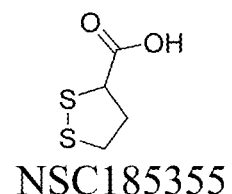
Figure 4:
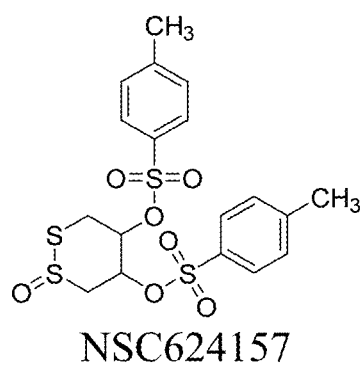
Figure 4:
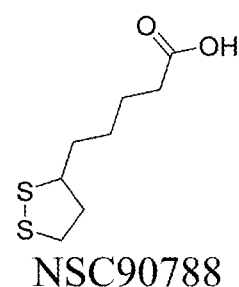
Figure 4:
Figure 4:
Figure 5:
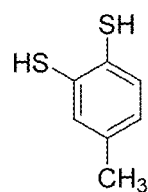
FIG. 5 depicts a dithiol that is able to form covalent dimers of SOD1.

LC-MS screen of cyclic disulfides with SOD1 reveals small molecules that covalently link SOD1 dimers. Compounds being evaluated were dissolved and incubated with recombinant human WT SOD1 (SEQ ID NO:2). Reactions were analyzed by LC-ESI-IonTrap-MS on a HCT Ultra ion trap (Bruker Daltonics, Billerica, Mass., USA). The resulting data was examined using DataAnalysis 3.4 (Bruker Daltonics Inc., Billerica, Mass., USA). Mass spectra were averaged across the retention times corresponding to when SOD1 was found to be eluting and Maximum Entropy Deconvolution was applied to the resulting average mass spectrum in order to determine the molecular weight of the uncharged species detected. Significant dithiol- and cyclic disulfide-mediated covalent dimer formation has been observed with multiple different compounds. For example, the changes in mass of the covalently linked SOD1 dimers observed suggest both 1,2-dithiolane-4,4-dimethanol and 1-oxo-1,2-dithiane (FIG. 2a) are capable of covalently dimerizing SOD1. Of note, 1-oxo-1,2-dithiane was able to cross-link the majority of SOD1 monomers in the sample (FIG. 2b) and the mass of the cross-linked SOD1 dimer corresponds to the loss of one water molecule after the addition of 1-oxo-1,2-dithiane to a SOD1 dimer. 1-oxo-1,2-dithiane (NSC56224) and its analogues have been partially characterized previously for their ability to attack retroviral zinc fingers. Identified compounds can be found in FIG. 4 and FIG. 5.

Example 3

Figure 3:
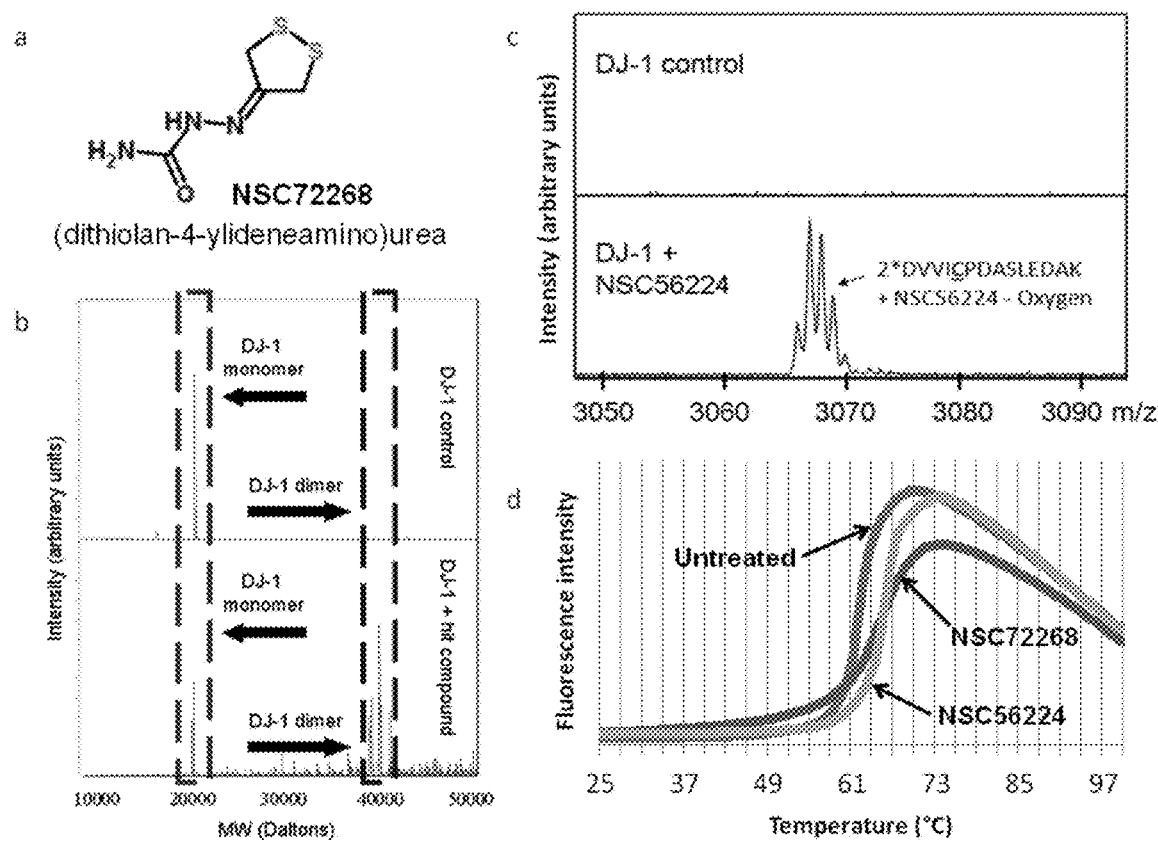
FIG. 3 depicts a preliminary LC-ESI-IonTrap-MS screen of cyclic disulfides that identifies compounds that form covalent DJ-1 dimers at Cys53 and increase the thermal stability of DJ-1. a) NSC72268 was identified as a specific covalent dimerizer of DJ-1. b) Deconvoluted spectra of untreated DJ-1 (top) and NSC72268-treated DJ-1. c) MALDI-TOF-MS spectra showing a detected ion specific for NSC56224-treated DJ-1 corresponding to two trypsin digest fragments of DJ-1 containing Cys53 (underlined) linked by NSC56224. d) NSC56224 and NSC72268 increase the measured denaturation temperature of DJ-1 relative to untreated DJ-1 (N=3, error bars not shown but standard deviation is less than thickness of lines).
Figure 6:
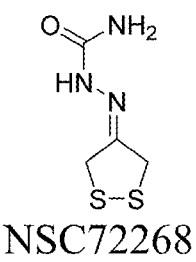
FIG. 6 depicts examples of cyclic disulfide compounds that are able to form covalent dimers of DJ-1.
Figure 6:
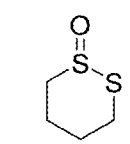

LC-MS screen of cyclic disulfides with DJ-1 reveals molecules that covalently link DJ-1 dimers. Using the same method as described for SOD1, compounds were screened against WT DJ-1. In addition to NSC56224 again being identified as a covalent dimerizer of DJ-1, NSC72268 was identified as a specific DJ-1 covalent dimerizer (FIG. 3a,b). Digesting NSC56224-linked DJ-1 with trypsin following by MALDI-TOF-MS confirmed NSC56224 covalently linked DJ-1 dimers at Cys53 (FIG. 3c). Both NSC56224 and NSC72268 were found to increase the denaturation temperature of DJ-1 measured with differential scanning fluorimetry (FIG. 3d) (Niesen et al., 2007), suggesting covalent dimerization increased DJ-1 thermal stability. NSC72268 and NSC56224 are shown in FIG. 6.

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method of treating a patient suffering from Amyotrophic Lateral Sclerosis (ALS), Parkinson's disease, or Alzheimer's disease, wherein said method comprises administering to the patient a stabilized superoxide dismutase (SOD1) dimer or a stabilized DJ-1 dimer, wherein said stabilized superoxide dismutase dimer has a tertiary structure and comprises a first SOD1 monomer and a second SOD1 monomer; wherein the first SOD1 monomer comprises a first cysteine residue; the second SOD1 monomer comprises a second cysteine residue, and wherein said first SOD1 monomer and said second SOD1 monomer is at least 85% sequence identity to the amino acid sequence of SEQ ID NO:2; or said stabilized DJ-1 dimer has a tertiary structure and comprises a first DJ-1 monomer and a second DJ-1 monomer; wherein the first DJ-1 monomer comprises a first cysteine residue; the second DJ-1 monomer comprises a second cysteine residue, and wherein said first DJ-1 monomer and said second DJ-1 monomer Is at least 85% sequence identity to the amino acid sequence of SEQ ID NO:1; and wherein the first cysteine residue is connected to the second cysteine residue by a connection; and the connection is a connection of Formula III or Formula IV:

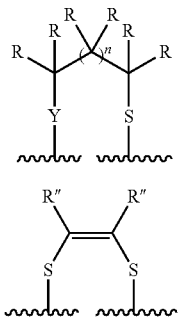

wherein
Y is S, S=O, or S(=O)2; n is 0, 1, 2, 3, or 4;
R is independently selected from the group consisting of —H, —OH, —NH$_2$, —NHR', —N(R')$_2$, alkyl, —OMs, —OTs, —OTf, and —CO$_2$H; or any two geminal R groups, taken together, form an imine; or any two vicinal R groups, taken together, form a ring; wherein any alkyl or imine may be substituted with a carbamide, a carboxylate, or a hydroxyl; and
R' is alkyl or aryl; and
R" is —H, alkyl, or aryl, or both R", taken together, form a ring; wherein any alkyl, aryl, or ring may be substituted with —OH, alkyl, or halo.

2. The method of claim 1, wherein said dimer is a stabilized superoxide dismutase dimer.

3. The method of claim 1, wherein said dimer is a stabilized DJ-1 dimer.

4. The method of claim 1, wherein said first SOD1 monomer and said second SOD1 monomer are different in amino acid sequence.

5. The method of claim 1, wherein said first SOD1 monomer and said second SOD1 monomer have the same amino acid sequence.

6. The method of claim 1, wherein the first SOD1 monomer of said dimer is the wild-type sequence of SEQ ID NO: 2.

7. The method of claim 1, wherein the first SOD1 monomer of said dimer comprises a mutation selected from the group consisting of G93A, G85R, D90A, A4V, E100G, H46R, C6G, and I113T of SEQ NO:2.

8. The method of claim 1, wherein the second SOD1 monomer of said dimer is the wild-type sequence of SEQ ID NO: 2.

9. The method of claim 1, wherein the second SOD1 monomer of said dimer comprises a mutation selected from the group consisting of G93A, G85R, D90A, A4V, E100G, H46R, C6G, and I113T of SEQ ID NO:2.

10. The method of claim 1, wherein said SOD1 retains at least 90% activity of the wild-type superoxide dismutase enzyme of SEQ ID NO: 2 up to a temperature of 75° C.

11. The method of claim 1, wherein said first DJ-1 monomer and said second DJ-1 monomer are different in amino acid sequence.

12. The method of claim 1, wherein said first DJ-1 monomer and said second DJ-1 monomer have the same amino acid sequence.

13. The method of claim 1, wherein said dimer retains at least 90% activity of the wild-type DJ-1 up to a temperature of 75° C.

14. The method of claim 3, wherein the connection is a connection of Formula III:

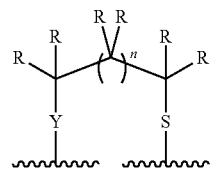

wherein Y is S, n is 2, and R is H.

15. The method of claim 3, wherein the first DJ-1 monomer of said dimer is the wild type DJ 1 of SEQ ID NO: 1.

16. The method of claim 2, wherein the connection is a connection of Formula III:

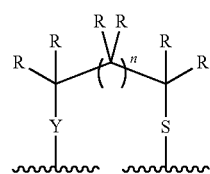

wherein Y is S, n is 2, and R is H.

* * * * *

SEQUENCE LISTING

```
<160> NUMBER OF SEQ ID NOS: 2

<210> SEQ ID NO 1
<211> LENGTH: 189
<212> TYPE: PRT
<213> ORGANISM: Homo sapiens

<400> SEQUENCE: 1

Met Ala Ser Lys Arg Ala Leu Val Ile Leu Ala Lys Gly Ala Glu Glu
1               5                   10                  15

Met Glu Thr Val Ile Pro Val Asp Val Met Arg Arg Ala Gly Ile Lys
            20                  25                  30

Val Thr Val Ala Gly Leu Ala Gly Lys Asp Pro Val Gln Cys Ser Arg
        35                  40                  45

Asp Val Val Ile Cys Pro Asp Ala Ser Leu Glu Asp Ala Lys Lys Glu
    50                  55                  60
```

```
Gly Pro Tyr Asp Val Val Leu Pro Gly Gly Asn Leu Gly Ala Gln
 65                  70                  75                  80

Asn Leu Ser Glu Ser Ala Ala Val Lys Glu Ile Leu Lys Glu Gln Glu
                 85                  90                  95

Asn Arg Lys Gly Leu Ile Ala Ala Ile Cys Ala Gly Pro Thr Ala Leu
                100                 105                 110

Leu Ala His Glu Ile Gly Cys Gly Ser Lys Val Thr Thr His Pro Leu
            115                 120                 125

Ala Lys Asp Lys Met Met Asn Gly Gly His Tyr Thr Tyr Ser Glu Asn
130                 135                 140

Arg Val Glu Lys Asp Gly Leu Ile Leu Thr Ser Arg Gly Pro Gly Thr
145                 150                 155                 160

Ser Phe Glu Phe Ala Leu Ala Ile Val Glu Ala Leu Asn Gly Lys Glu
                165                 170                 175

Val Ala Ala Gln Val Lys Ala Pro Leu Val Leu Lys Asp
                180                 185

<210> SEQ ID NO 2
<211> LENGTH: 154
<212> TYPE: PRT
<213> ORGANISM: Homo sapiens

<400> SEQUENCE: 2

Met Ala Thr Lys Ala Val Cys Val Leu Lys Gly Asp Gly Pro Val Gln
  1               5                  10                  15

Gly Ile Ile Asn Phe Glu Gln Lys Glu Ser Asn Gly Pro Val Lys Val
                 20                  25                  30

Trp Gly Ser Ile Lys Gly Leu Thr Glu Gly Leu His Gly Phe His Val
             35                  40                  45

His Glu Phe Gly Asp Asn Thr Ala Gly Cys Thr Ser Ala Gly Pro His
 50                  55                  60

Phe Asn Pro Leu Ser Arg Lys His Gly Gly Pro Lys Asp Glu Glu Arg
 65                  70                  75                  80

His Val Gly Asp Leu Gly Asn Val Thr Ala Asp Lys Asp Gly Val Ala
                 85                  90                  95

Asp Val Ser Ile Glu Asp Ser Val Ile Ser Leu Ser Gly Asp His Cys
                100                 105                 110

Ile Ile Gly Arg Thr Leu Val Val His Glu Lys Ala Asp Asp Leu Gly
            115                 120                 125

Lys Gly Gly Asn Glu Glu Ser Thr Lys Thr Gly Asn Ala Gly Ser Arg
130                 135                 140

Leu Ala Cys Gly Val Ile Gly Ile Ala Gln
145                 150
```